(12) United States Patent
Skender (10) Patent No.: US 9,907,680 B2
(45) Date of Patent: Mar. 6, 2018

(54) SLIDING FENESTRATION

(71) Applicant: Cook Medical Technologies LLC, Bloomington, IN (US)

(72) Inventor: Davorin Kevin Skender, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/091,685

(22) Filed: Apr. 6, 2016

(65) Prior Publication Data
US 2016/0296353 A1 Oct. 13, 2016

Related U.S. Application Data

(60) Provisional application No. 62/145,822, filed on Apr. 10, 2015.

(51) Int. Cl.
*A61F 2/07* (2013.01)
*A61F 2/856* (2013.01)
*A61F 2/06* (2013.01)

(52) U.S. Cl.
CPC .............. *A61F 2/856* (2013.01); *A61F 2/07* (2013.01); *A61F 2002/061* (2013.01); *A61F 2002/075* (2013.01); *A61F 2230/005* (2013.01); *A61F 2230/006* (2013.01); *A61F 2230/0019* (2013.01); *A61F 2230/0069* (2013.01); *A61F 2250/006* (2013.01); *A61F 2250/0039* (2013.01)

(58) Field of Classification Search
CPC ........... A61F 2/07; A61F 2002/065–2002/067; A61F 2/82

USPC ................. 623/1.35–1.48, 1.1–1.15
See application file for complete search history.

(56) References Cited

U.S. PATENT DOCUMENTS

| | | | | |
|---|---|---|---|---|
| 6,663,667 | B2 * | 12/2003 | Dehdashtian | A61F 2/07 623/1.35 |
| 2005/0059923 | A1 * | 3/2005 | Gamboa | A61F 2/07 604/9 |
| 2006/0287704 | A1 * | 12/2006 | Hartley | A61F 2/07 623/1.13 |
| 2008/0091263 | A1 * | 4/2008 | Iyer | A61K 9/0024 623/1.42 |
| 2008/0114446 | A1 * | 5/2008 | Hartley | A61F 2/07 623/1.13 |

(Continued)

FOREIGN PATENT DOCUMENTS

| | | |
|---|---|---|
| EP | 1 759 660 A1 | 3/2007 |
| WO | WO 2004/026181 A1 | 4/2004 |

(Continued)

OTHER PUBLICATIONS

Extended European Search Report in corresponding European Application No. 16275050.9, dated Jun. 21, 2016, 7 pages.

*Primary Examiner* — Suzette J Gherbi
(74) *Attorney, Agent, or Firm* — Brinks Gilson & Lione (57) ABSTRACT

A prosthesis comprising a graft having a tubular body with a wall defining an external surface of the graft and a pouch. The graft further comprises a strip with at least one fenestration, wherein the strip is at least partially contained within the pouch. A window may be formed within the wall, wherein the fenestration is at least partially aligned with the window, thereby forming a channel through the fenestration and the window.

20 Claims, 6 Drawing Sheets

(56) References Cited

U.S. PATENT DOCUMENTS

| | | | | |
|---|---|---|---|---|
| 2009/0216315 A1* | 8/2009 | Schreck | .................... | A61F 2/07 623/1.35 |
| 2009/0259290 A1* | 10/2009 | Bruszewski | .............. | A61F 2/07 623/1.13 |
| 2014/0249614 A1* | 9/2014 | Levi | ................ | A61B 17/12022 623/1.11 |
| 2014/0277347 A1* | 9/2014 | Daugherty | .............. | A61F 2/856 623/1.11 |
| 2017/0007392 A1* | 1/2017 | Louren | .................... | A61F 2/07 |
| 2017/0135806 A1* | 5/2017 | Ombrellaro | ............... | A61F 2/07 |

FOREIGN PATENT DOCUMENTS

| | | |
|---|---|---|
| WO | WO 2005/034809 A1 | 4/2005 |
| WO | WO 2014/149531 A1 | 9/2014 |

* cited by examiner

SLIDING FENESTRATION

PRIORITY

This application claims priority to U.S. Provisional Patent Application No. 62/145,822, filed on Apr. 10, 2015, entitled "SLIDING FENESTRATION," the entire disclosure of which is herein incorporated by reference.

BACKGROUND

The functional vessels of human and animal bodies, such as blood vessels and ducts, occasionally weaken or even rupture. For example, the aortic wall can weaken, resulting in an aneurysm, or it may develop a tear in one of the layers of the aortic wall resulting in an aortic dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules. They also may be a single tubular device or a bifurcated branching device depending on the desired application.

In many cases, however, the damaged or defective portion of the vasculature may include a branch vessel branching from the main vessel. For example, in the case of the abdominal aorta, there are at least three major branch vessels, including the celiac, mesenteric, and renal arteries, as well as others, leading to various other body organs. Thus, when the damaged portion of the vessel includes one or more of these branch vessels, some accommodation must be made to ensure that the prosthesis does not block or hinder blood flow through the branch vessel. In many instances, there may be insufficient healthy tissue in the aorta near the branching vessels adequately seal a prosthesis without partially or completely blocking one or more of the branching vessels.

BRIEF SUMMARY

This application is directed at a prosthesis comprising a graft having a tubular body, a wall defining an external surface of the graft, and a pouch, the prosthesis may have a strip with at least one fenestration. In one embodiment, the strip is at least partially contained within the pouch. A window may be formed within the wall, and the fenestration may be at least partially aligned with the window thereby forming a channel through the fenestration and the window. The channel may be formed from internally to externally of the tubular body.

In one embodiment, the prosthesis further comprises a branch prosthesis extending distally of the fenestration. The strip may be slidable axially within the pouch, thereby moving the fenestration axially to adapt to the geometry of a branch vessel. Further, the strip may be slidable radially within the pouch. The strip may be shaped as a substantially circular disk.

The pouch may comprise a first internal surface and a second internal surface. In one embodiment, the strip may be clamped between the first internal surface and the second internal surface. Further, an outer perimeter of the strip may entirely cover an outer perimeter of the window when the strip is in any position within the pouch.

DETAILED DESCRIPTION

The present disclosure relates to an endoluminal prosthesis, such as a stent graft that includes one or more fenestrations to accommodate endovascular disease, such as an aneurysm in cases where one or more side branches is involved. In one embodiment, the prosthesis includes slidable fenestrations that slide as needed to accommodate the dynamic geometry of the aortic branches.

Definitions

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow.

The term "proximal" means a location or direction that is, or a portion of a device that when implanted is further upstream in the direction of or with respect to blood flow.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyamids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may be constructed from natural or organic materials, for example and without limitation, a biological scaffold or bioremodelable material, such as small intestine submucosa ("SIS"), which is commercially available by Cook Biotech, West Lafayette, Ind. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents 16 may be comprised of a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide (Li2O3), and a nickel-titanium alloy, such as nitinol, or other suitable materials as known in the art. The stents may be made of a wire, or may be laser or cannula cut, or manufactured by other known methods.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

Figure 1:
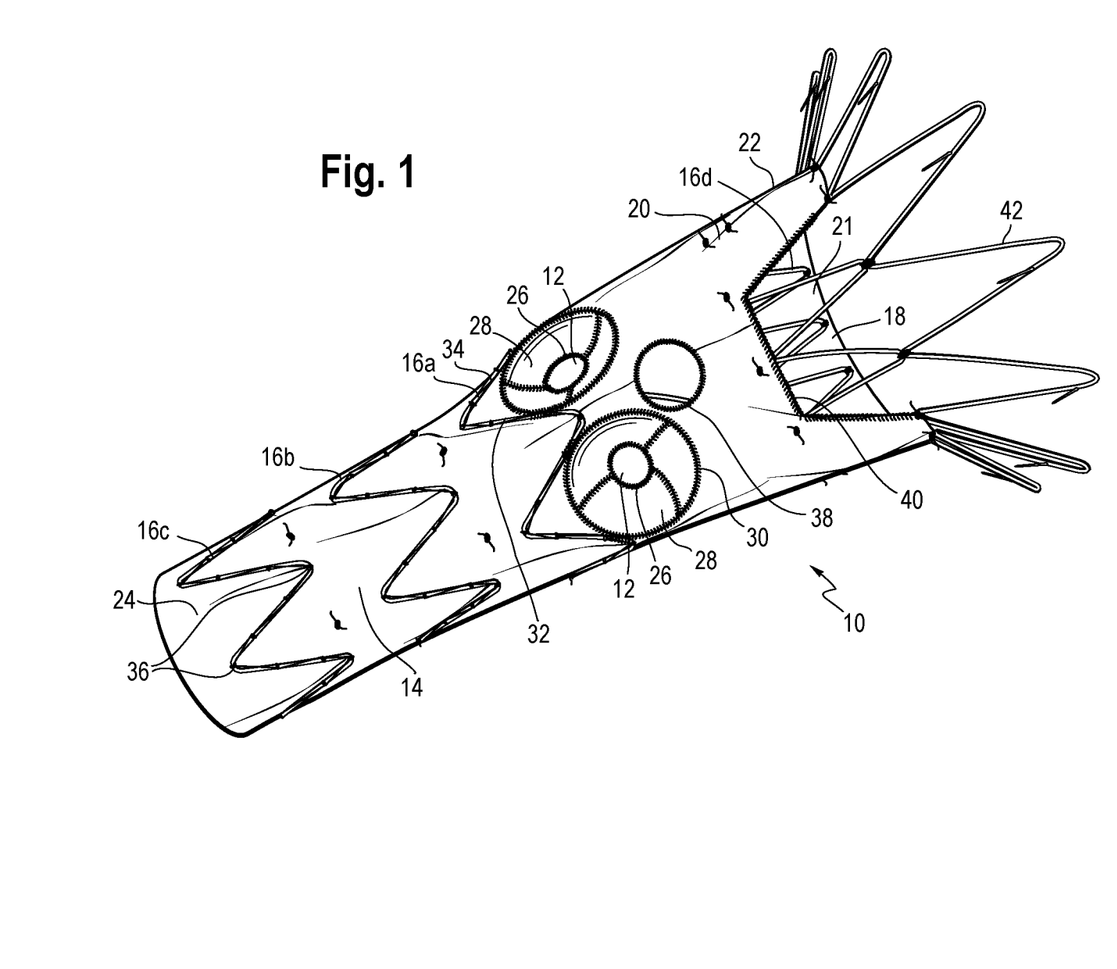
FIG. 1 shows a perspective view of a fenestrated prosthesis with pivotable fenestrations.

FIG. 1 shows a perspective view of a prosthesis 10 that is a stent graft. The prosthesis 10 includes graft material 14 associated with one or more stents 16. The prosthesis 10 has a proximal end 22, a distal end 24, and a lumen 18 extending through the prosthesis 10 to permit passage of blood flow from the proximal end 22 to the distal end 24. The stents 16 may be placed on the external surface 20 and/or internal surface 21 of the graft material 14. In one particular embodiment, the prosthesis 10, such as that shown in FIG. 1, has external body stents 16a, 16b, and 16c, and at least one internal stent 16d. The internal stent 16d may be a sealing stent and placed at or near the proximal end 22 of the prosthesis 10 to seal the prosthesis 10 at the proximal end 22 to the walls of a blood vessel into which it has been placed. Additionally, or alternatively, depending on the location of the place of the prosthesis 10 or a particular need, a sealing stent 16d may be placed at either or both the proximal and distal ends 22, 24 of prosthesis 10. The prosthesis 10 also may include an attachment mechanism, for example, an attachment stent 42, at either or both ends of the prosthesis 10, to further secure the prosthesis 10 within the body vessel and prevent migration of the prosthesis 10.

As shown in FIG. 1, the prosthesis 10 has multiple openings or fenestrations that extend from the internal surface 21 to the external surface 20 of the graft material 14. The prosthesis 10 of FIG. 1 has two pivotable fenestrations 12, at least one non-pivotable fenestration 38, and a scallop 40. Here, the scallop 40 is placed at the proximal end of the prosthesis 10.

Stents 16, for example those shown in the FIG. 1, may be, for example zig zag stents, also known has Z-stents, that comprise a series of struts 32, 34 connected by apices 36, although the type of stent used is not so limited. When Z-stents are used, a portion of the outer perimeter 30 of one or more of the fenestrations 12 may lie between adjacent struts 32, 34 of one of the stents 16. The stents 16 may be either self-expanding or balloon expandable. Preferably, they are self-expanding. However, a combination of self-expanding and balloon expandable stents also may be contemplated.

As set forth above, the stents 16 include struts 32, 34 that are spaced apart from each other. The strut spacing is measured from bend-to-bend (or apex to apex 36). Stent amplitude, spacing and stagger are preferably optimized for each prosthesis design. In some aspects, the apices or bends 36 of the struts 32, 34 may be staggered for minimal contact with each other. As shown in FIG. 1, the stents 16a, 16b, 16c are positioned adjacent each other and the apices 36 of each row are in circumferential alignment with the bends of longitudinally adjacent rows. In other aspects, every bend 36 of each row may be in substantial circumferential alignment with the bends 36 of longitudinally adjacent rows.

Figure 2:
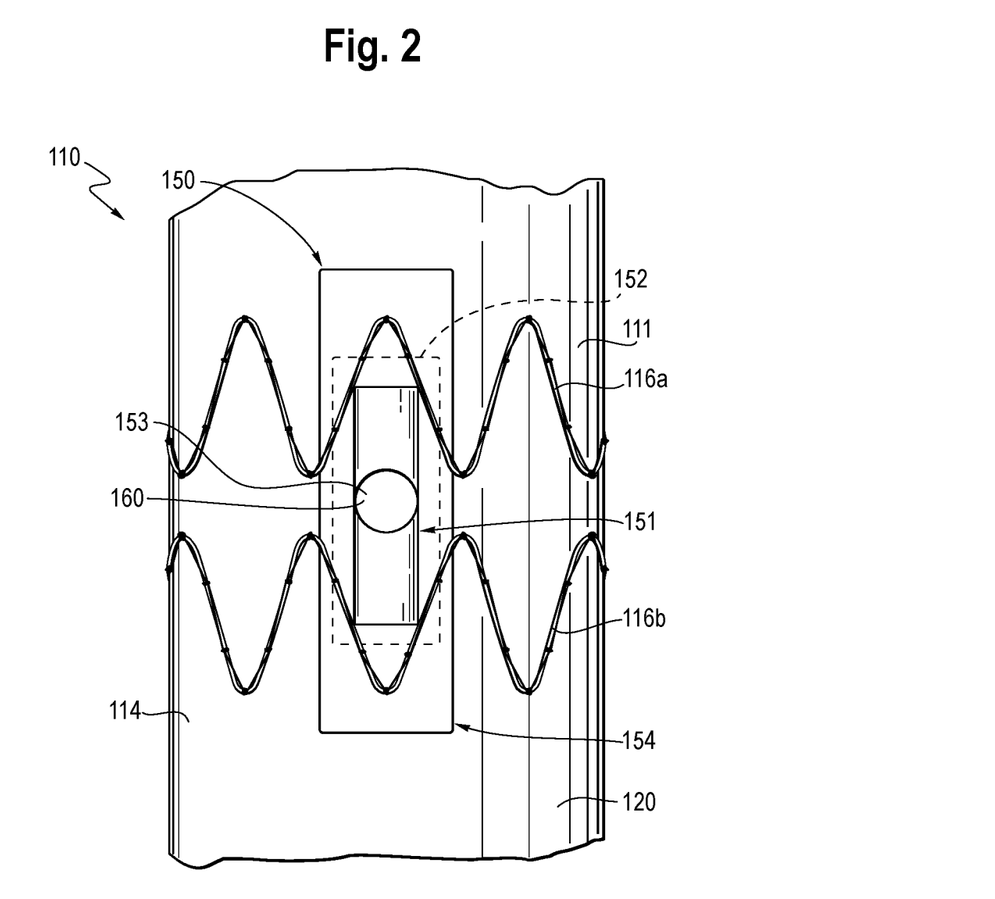
FIG. 2 is a front view of a portion of a prosthesis with a sliding fenestration system having a sliding strip.

FIG. 2 shows a front view of a portion of an alternative prosthesis 110 that is a stent graft. The prosthesis 110 may comprise some of the features of the embodiment of the prosthesis 10, with like reference numerals designating like parts, and main differences of the embodiment of FIGS. 2-3 explained further below. Prosthesis 110 comprises a tubular body 111 having an external wall 120 made of stent graft material 114, stents 116a and 116b, and sliding fenestration system 150. In one embodiment, sliding fenestration system 150 comprises a sliding strip 152. Sliding strip 152 may a fenestrated strip of material at least partially contained within a pouch 154, and may be adapted to move or slide in an axial direction distally and/or proximally within pouch 154. Pouch 154 may be formed within wall 120 and may remain substantially stationary with respect to tubular body 111 during normal operation. It may be assembled by stitching one or more strips of material to tubular body 111. Pouch 154 may be located internally and/or externally of tubular body 111. In one embodiment, pouch 154 is formed within wall 120 as depicted by FIG. 3.

Sliding strip 152 is preferably fenestrated, preferably comprising at least one fenestration 153. Referring to FIG. 2, sliding strip 152 is preferably in communication with a window 151, which may be an aperture or opening formed within external wall 120 and/or tubular body 111. In one embodiment, as depicted by FIG. 2, window 151 comprises a substantially rectangular opening in wall 120, where the lengthwise direction of the rectangle runs parallel with the longitudinal axis of prosthesis 110. However, window 151 is not limited to any particular shape or directional orientation. Sliding strip 152 is preferably positioned with respect to window 151 such that fenestration 153 is at least partially selectively aligned with window 151, thereby forming a channel 160 from internal to external of tubular body 111.

In one embodiment, the width of sliding strip 152 may be substantially equal to or slightly less than the width of pouch 154. The axial length of sliding strip 152 may be smaller than the axial length of pouch 154. These dimensions may allow sliding strip 152 to move axially in either or both of the distal and proximal directions within pouch 154 and with respect to window 151, such that fenestration 153 is adaptable to the geometry of a target branch vessel axially, but is substantially prevented from moving radially. In one embodiment, fenestration 153 remains at least partially aligned with window 151 in all positions during normal operation. Sliding strip 152 is preferably sized such that it covers substantially all of window 151 other than intended channels, such as channel 160, during normal operation, thereby preventing unwanted leakage through window 151.

Figure 3A:
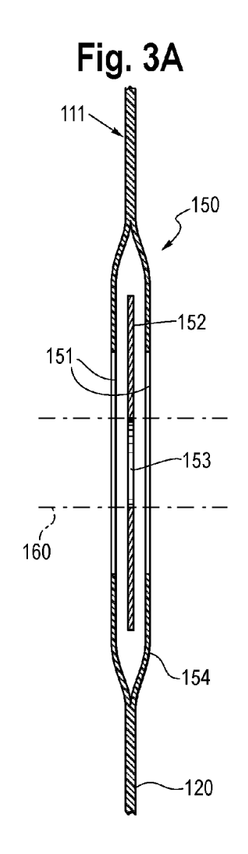
FIGS. 3A-3C depict a cross-sectional profile view of a portion of the prosthesis of FIG. 2 with the sliding strip in different positions.
Figure 3B:
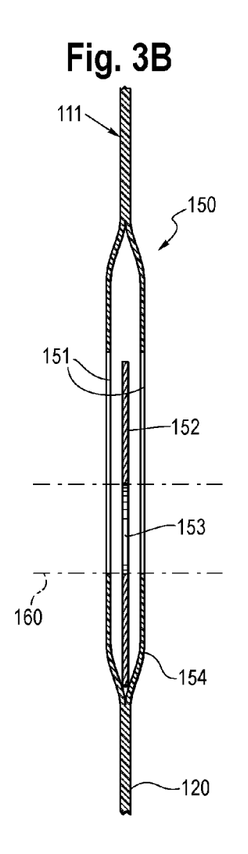
Figure 3C:
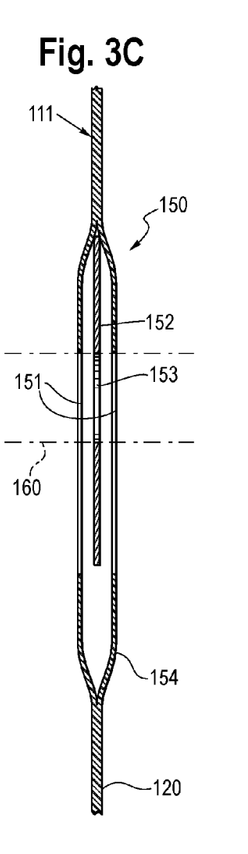

FIG. 3A shows a profiled view of sliding strip fenestration system 150 with a sliding strip 152 in a first position. In one embodiment, as depicted by FIGS. 3A-C, sliding strip 152 is contained within pouch 154, which is formed within wall 120. Pouch 154 is preferably sized such that it allows sliding strip 152 to move axially to thereby allow fenestration 153 to adapt to different dynamic geometries of target branch vessels, and also sized to ensure fenestration 152 remains aligned with window 151. Channel 160 may run from internal to external of tubular body 111, and preferably is adapted to receive a branch prosthesis during normal operation.

In FIG. 3A, sliding strip 152 is located in a first position such that fenestration 153 is approximately centered within window 151 and with respect to the axial direction, thereby creating channel 160 passing through approximately the axial center of window 151 from internal to external of tubular body 111. Sliding strip may be capable of moving axially within pouch 154. For example, sliding strip 152 may move axially in the distal direction such that it is located in a second position as depicted by FIG. 3B. In the second position, sliding strip 152 may be located within pouch 154 such that fenestration 153 is located distally of the axial center of window 151, thereby forming channel 160 running from internal to external of tubular body 111 through a portion of window 151 that is located distally of the axial center of window 151. Similarly, sliding strip 152 may be adaptable to move to a third position, for example the position depicted by FIG. 3C. FIG. 3C depicts sliding strip 152 positioned such that fenestration 153 is located proximally of the axial center of window 151. In this position, channel 160 may run from internally to externally from of tubular body 111 through a portion of window 151 that is located proximally of the axial center of window 151. The examples described herein are non-limiting, and there is no particular significance to a position corresponding to the axial center of window 151, which is used only as a reference-point to illustrate and describe the functionality of the current embodiment.

Figure 4:
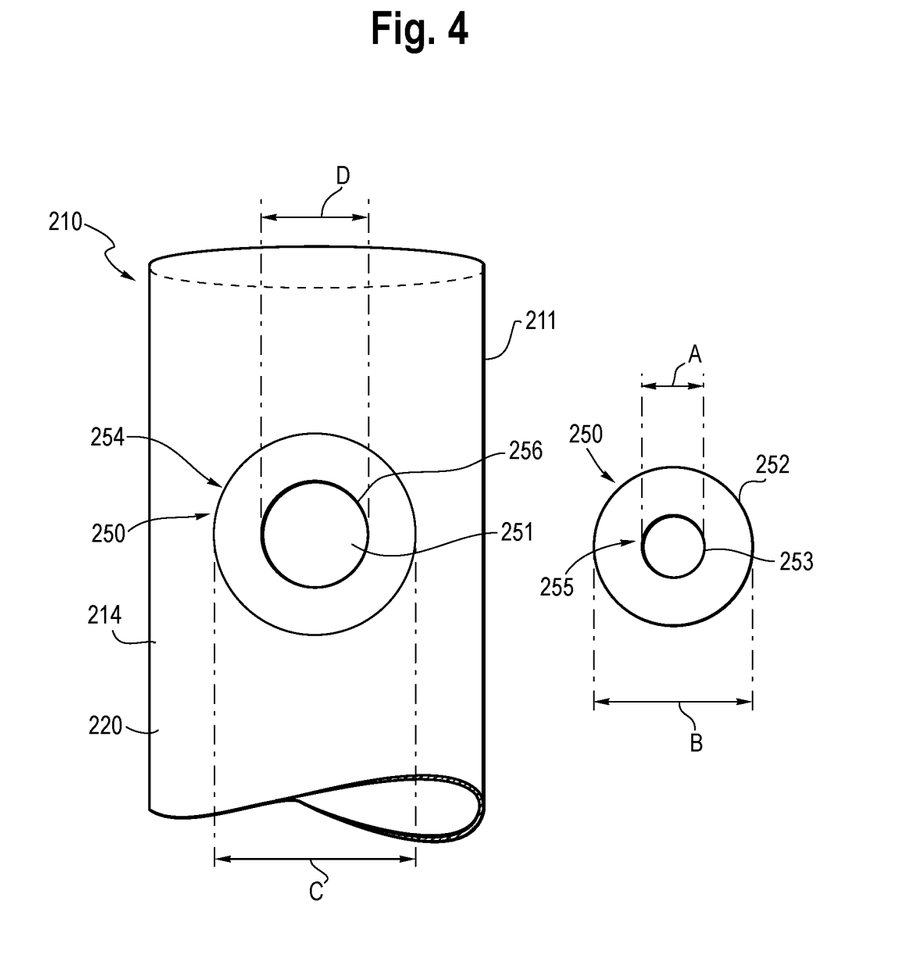
FIG. 4 is a front, partially exploded view of an alternative prosthesis with a sliding fenestration system having a sliding disk.
Figure 6:
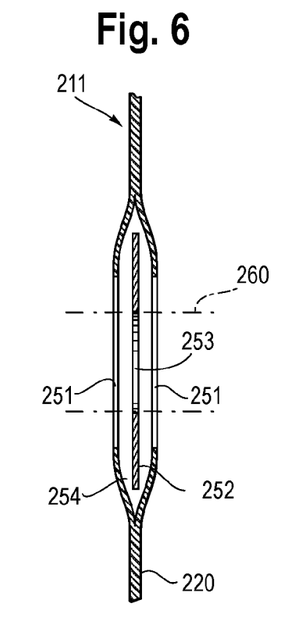
FIG. 6 is a cross-sectional profile view of a portion of the prosthesis of FIGS. 4-5.

FIG. 4 shows a front, partially exploded view of an alternative prosthesis 210. Referring to FIG. 4, prosthesis 210 is a stent graft with a tubular body 211 and an external wall 220 made of stent graft material 214. Sliding fenestration system 250 (shown exploded) may comprise a sliding strip of material which, as shown in FIG. 4, may be shaped as a sliding disk 252 (although it is not limited to any particular shape). Sliding disk 252 may be a fenestrated strip of material at least partially contained within a pouch 254, and may be adapted to move or slide within pouch 254. Pouch 254 is preferably defined within wall 220 of prosthesis 210 such that it is substantially stationary with respect to tubular body 211 during normal operation. It may be assembled by stitching one or more strips of material to tubular body 211. Pouch 254 may be located internally and/or externally of tubular body 211. In one embodiment, pouch 254 is formed within wall 220 as depicted by FIG. 6.

Sliding disk 252 is preferably fenestrated and preferably comprises at least one fenestration 253. Sliding disk 252 may communicate with a window 251, which may be an aperture or opening formed within external wall 220 and/or tubular body 211. In one embodiment, as depicted by FIG. 4, window 251 comprises a substantially circular opening in wall 220, but it is not limited to any particular shape. During normal operation, sliding disk 252 is preferably positioned with respect to window 251 such that fenestration 253 is at least partially aligned with window 251, thereby forming a channel from internal to external of tubular body 211.

Figure 5:
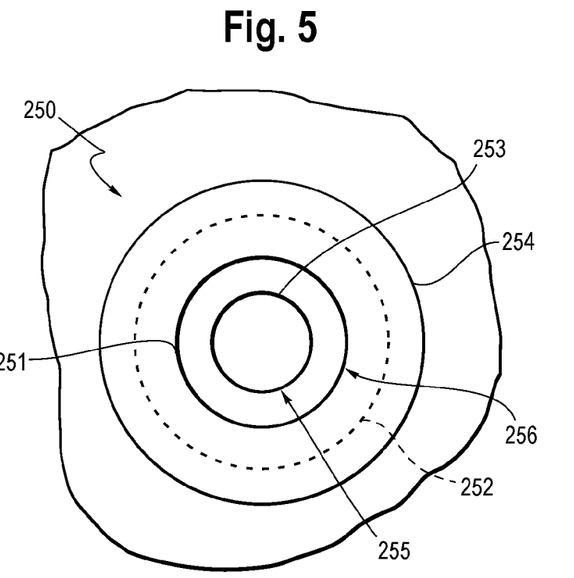
FIG. 5 is a front view of the sliding fenestration system of FIG. 4.

Fenestration 253 is preferably shaped such that it may receive a branch prosthesis to communicate with a target branch vessel. In one embodiment, as depicted by FIGS. 4-5, fenestration 253 may be substantially circular, but it is not limited to any particular shape. The outer edge of fenestration 253 may additionally be lined with a reinforcing ring 255. In one embodiment, reinforcing ring 255 may be attached through the use of a suture or stitching, but any attachment means now known or later developed may be used. Any type of reinforcing device may be used. Similarly, the outer edge of window 251 may comprise a reinforcing ring 256 or other reinforcing device.

In the embodiment depicted by FIG. 4, a diameter A of fenestration 253 is substantially smaller than diameter D of window 251. These dimensions ensure that the window 251 has an area that provides enough coverage of potential positions such that fenestration 253 can move to accommodate the dynamic geometry of the target branch vessel while remaining at least partially aligned with window 251. To prevent leakage through unintended areas or openings through window 251 (i.e., channels other than through one or more intended fenestrations such as fenestration 253), diameter B of sliding disk 252 is preferably substantially larger than the diameter D of window 251. In other words, sliding disk 252 is sized to provide substantial coverage over window 251 for multiple positions of fenestration 253. These dimensions further provide assurance that sliding disk 253 does not fall out of pouch 254 through window 251. Finally, diameter C of the pouch is preferably substantially larger than the diameter B of sliding disk 252. This provides sliding disk 252 the freedom to move to adapt to the dynamic geometry of a target branch vessel.

FIG. 5 shows a front view of the sliding disk fenestration system 250 of FIG. 4. In this embodiment, sliding disk 252 is contained within pouch 254. Sliding disk 252 comprises fenestration 253 and is sized with respect to pouch 254 such that it can move either axially or radially, thereby moving fenestration 253 either axially or radially. Fenestration preferably remains at least partially aligned with window 251 during normal operation. Fenestration 253 may have a reinforcing ring 255 as described above. Similarly, window 251 may comprise a reinforcing ring 256.

FIG. 6 shows a cross-sectional view of wall 220 comprising pouch 254. In the depicted embodiment, pouch 254 contains sliding disk 252. Sliding disk 252 comprises at least one fenestration 253. Window 251 comprises an opening in wall 220 such that a channel 260 is formed, passing from internal to external of tubular body 211 through fenestration 253 and window 251. Sliding disk 252 may block the portion of window 251 that is not aligned with fenestration 253, thereby preventing leakage from internal to external of tubular body 211.

Similar to the sliding strip 152 depicted in FIGS. 3A-3C, sliding disk 252 depicted by FIGS. 5-6 may be capable of moving to multiple positions within pouch 254. Sliding disk 252 may be capable of moving in the axial direction either distally or proximally thereby moving fenestration 253 and channel 260 distally or proximally. Further, as described above, pouch 254 is preferably shaped such that sliding disk 252 may also move radially. Channel 260 may pass through any portion of window 251.

Figure 7:
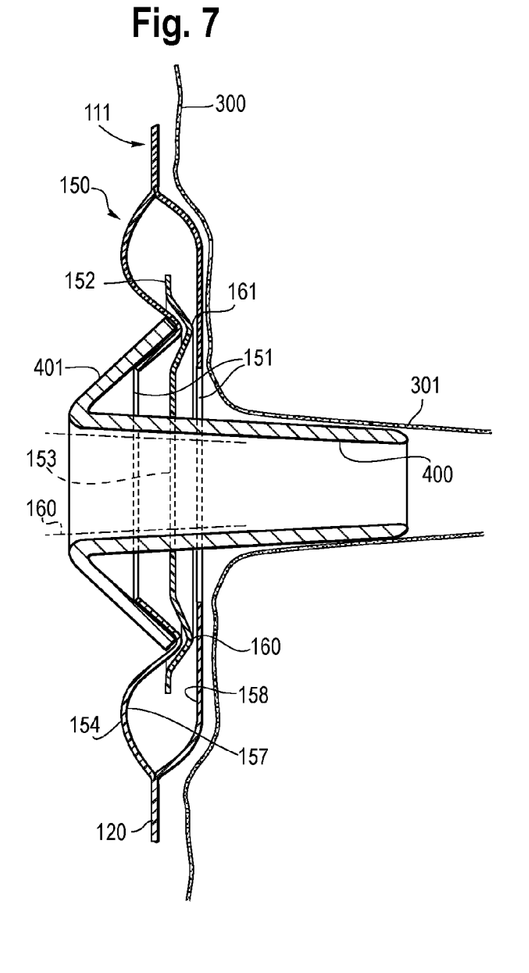
FIG. 7 is a cross-sectional profile view of a prosthesis with a sliding fenestration system installed within a patient and including a branch prosthesis.

FIG. 7 shows a fenestration system 150 located within a patient. In the depicted embodiment, the axial length of tubular body runs parallel with the axial length of a main vessel 300, which may be the patient's aorta. Branch vessel 301 branches off main vessel 300, and may, for example, be a celiac or a renal artery. In the depicted embodiment, fenestration system 150 comprises a sliding strip 152 and a pouch 154. Sliding strip 150 may move axially and/or radially within pouch 154 and may comprise a sliding disk similar to the embodiments described above. Channel 160 is formed from externally to internally of tubular body 111 through window 151 and fenestration 153. In the depicted embodiment, a branch prosthesis 400 is deployed into branch vessel 301. Branch prosthesis 400 is installed through the window 151 and fenestration 153. Branch prosthesis 400 may be a branch graft or branch stent graft as disclosed by U.S. Patent Application Publication No. 2005/0171598 A1 ("Schaeffer"), which is incorporated herein in its entirety.

Branch prosthesis 400 may be installed, for example, with the use of a delivery system including a moveable guide wire or catheter adapted to advance branch prosthesis 400 through window 151 and fenestration 153. In the embodiment depicted by FIG. 7, at least a portion of branch prosthesis is located internally of tubular body 111 and at least a portion of branch prosthesis 400 is located externally of tubular body 111. Branch prosthesis 400 may include a flaring portion 401, which may be located at the proximal end of branch prosthesis 400. The outer circumference of flaring portion 401 may be larger than the circumference of window 151 and/or fenestration 153, thereby limiting the distal deployment of branch prosthesis 400. In one embodiment, flaring portion 401 includes a holding device, such as a barb, for securing branch prosthesis 400 to an inner surface of tubular body 111, such as a surface of wall 120 and/or pouch 154 facing internally of tubular body 111. A tubular portion at the distal end of branch prosthesis 400 may also include a holding device, such as a barb, for securing branch prosthesis 400 to a wall of branch vessel 301.

Flaring portion 401 may be adapted to press against a side of pouch 154 internal of tubular body 111, as depicted in FIG. 7. In this embodiment, sliding strip 152 is clamped between wall 157 and wall 158 of pouch 154. In this embodiment, a seal may be created at the point of contact between walls 157, 158, and sliding strip 152. The seal formed at this point of contact may, for example, prevent fluids from flowing around sliding strip 152 in pouch 154. In some embodiments, sliding strip 152 may still able to move axially and/or radially notwithstanding being clamped at this point of contact.

Figure 8:
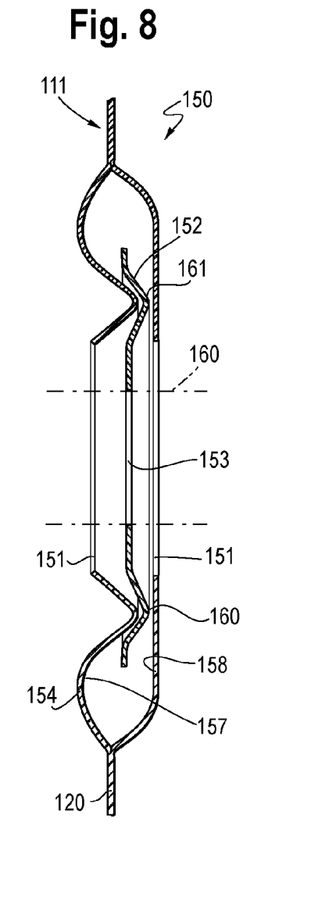
FIG. 8 is a cross-sectional profile view of the prosthesis of FIG. 7 where the patient and branch prosthesis are not shown.

FIG. 8 shows the sliding disk fenestration system as installed in FIG. 7. For illustrative purposes, the vessels of the patient 300, 301 and branch prosthesis 400 are not shown. As depicted by FIG. 8, sliding strip 152 is clamped at a point of contact 160 between wall 157 and wall 158 of pouch 154. Point of contact 160 may create a seal, thereby preventing leakage from internally to externally (or externally to internally) of tubular body 111.

The embodiments described herein are advantageous over prior devices in several respects. For example, a prosthesis with a sliding fenestration system is advantageous due to its ability to adapt to the variance in the positioning of diseased branch vessels. The described devices allow for flexibility in positioning of openings or fenestrations such that one device is capable of adapting to accommodate the dynamic geometries of branch vessels. Fenestration reposition or position adaptation is possible. For example, if a body branch vessel is or becomes offset longitudinally or axially from a fenestration 153, 253 (as depicted by FIGS. 2-6), fenestrations 153, 253 may slide with the branch vessel in the necessary direction and to the necessary degree to maintain the branch vessel prosthesis in place.

The described embodiments may have a greater degree of freedom and flexibility than prior devices. A movable disk or strip with at least one fenestration allows the main graft to move while still maintaining a perfectly aligned fenestration and connection stent without guillotining the connection stent during settling of the main graft. Further, a single prosthesis as described herein may be adaptable to a variety of patients and diseases, and therefore may drive down medical costs with respect to low-volume prosthesis devices.

Throughout this specification, various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention

The invention claimed is:

1. A prosthesis, the prosthesis comprising:
a graft having a tubular body, a wall defining an external surface of the graft, and a pouch;
a strip comprising at least one fenestration, wherein the strip is at least partially contained within the pouch; and
a window formed within the wall,
wherein the fenestration is at least partially aligned with the window thereby forming a channel through the fenestration and the window.

2. The prosthesis of claim 1 further comprising a branch prosthesis extending at least partially distally of the fenestration.

3. The prosthesis of claim 1, wherein the strip is slidable axially within the pouch.

4. The prosthesis of claim 3, wherein the strip is slidable radially within the pouch.

5. The prosthesis of claim 4, wherein the strip is shaped as a substantially circular disk.

6. The prosthesis of claim 2, wherein the pouch comprises a first internal surface and a second internal surface, and wherein in a deployed state, the strip is clamped between the first internal surface and the second internal surface.

7. The prosthesis of claim 1, wherein an outer perimeter of the strip entirely covers an outer perimeter of the window when the strip is in any position within the pouch.

8. The prosthesis of claim 1, wherein the channel is formed from internally to externally of the tubular body.

9. A prosthesis, the prosthesis comprising:
a graft having a tubular body and comprising an external wall and at least one window;
a pouch; and
a sliding strip at least partially contained within the pouch, movable with respect to the pouch, and having at least one fenestration.

10. The prosthesis of claim 9, wherein the sliding strip is movable axially within the pouch.

11. The prosthesis of claim 10, wherein the sliding strip is movable radially within the pouch.

12. The prosthesis of claim 9, wherein the fenestration is at least partially aligned with the window.

13. The prosthesis of claim 12, wherein the prosthesis further comprises a channel from internal to external of the tubular body through the fenestration and the window.

14. The prosthesis of claim 13, wherein the channel is adapted to receive a branch prosthesis.

15. The prosthesis of claim 14, wherein a flaring portion of the branch prosthesis 14 is adapted to press against a side of the pouch to clamp the sliding strip within the pouch.

16. A method of effecting an endoluminal vascular repair comprising:
deploying a prosthesis comprising a tubular body, a pouch with a window, and a strip having a fenestration, wherein the strip is at least partially contained within the pouch, and wherein the fenestration is at least partially aligned with the window; and
sliding the strip from a first position to a second position.

17. The method of claim 16 further comprising sliding the strip radially within the pouch.

18. The method of claim 16 further comprising deploying a branch prosthesis through the window and the fenestration.

19. The method of claim 16 further comprising clamping the strip within the pouch.

20. The method of claim 16 further comprising forming a seal within the pouch.

\* \* \* \* \*